(12) United States Patent
Curran et al.

(10) Patent No.: US 8,805,900 B2
(45) Date of Patent: Aug. 12, 2014

(54) METHODS, APPARATUSES AND COMPUTER PROGRAM PRODUCTS FOR FACILITATING LOCATION AND RETRIEVAL OF HEALTH INFORMATION IN A HEALTHCARE SYSTEM

(75) Inventors: Charles Curran, Pinole, CA (US); Susannah D'Oench, San Francisco, CA (US)

(73) Assignee: McKesson Financial Holdings, Hamilton (BM)

( * ) Notice: Subject to any disclaimer, the term of this patent is extended or adjusted under 35 U.S.C. 154(b) by 0 days.

(21) Appl. No.: 13/436,176

(22) Filed: Mar. 30, 2012

(65) Prior Publication Data

US 2013/0262474 A1 Oct. 3, 2013

(51) Int. Cl.
*G06F 7/00* (2006.01)
(52) U.S. Cl.
USPC ............................................. 707/822
(58) Field of Classification Search
USPC .......................................... 707/758
See application file for complete search history.

(56) References Cited

U.S. PATENT DOCUMENTS

| | | | |
|---|---|---|---|
| 5,991,758 A | 11/1999 | Ellard | |
| 5,999,937 A | 12/1999 | Ellard | |
| 6,397,224 B1 | 5/2002 | Zubeldia et al. | |
| 6,496,838 B1 | 12/2002 | Zamora-McKelvy et al. | |
| 6,523,019 B1 | 2/2003 | Borthwick | |
| 6,912,549 B2 | 6/2005 | Rotter et al. | |
| 6,922,695 B2 | 7/2005 | Skufca et al. | |
| 6,978,268 B2 | 12/2005 | Thomas et al. | |
| 6,996,565 B2 | 2/2006 | Skufca et al. | |
| 7,167,858 B2 | 1/2007 | Naeymi-Rad et al. | |
| 7,318,059 B2 | 1/2008 | Thomas et al. | |
| 7,376,677 B2 | 5/2008 | Ober et al. | |
| 7,523,505 B2 | 4/2009 | Menschik et al. | |
| 7,526,486 B2 | 4/2009 | Cushman, II et al. | |
| 7,620,647 B2 | 11/2009 | Stephens et al. | |
| 7,627,550 B1 | 12/2009 | Adams et al. | |
| 7,685,093 B1 | 3/2010 | Adams et al. | |
| 7,698,268 B1 | 4/2010 | Adams et al. | |
| 7,707,047 B2 | 4/2010 | Hasan et al. | |
| 7,725,331 B2 | 5/2010 | Schurenberg et al. | |
| 7,801,878 B2 | 9/2010 | Hayes et al. | |
| 7,941,328 B2 | 5/2011 | Castille | |
| 8,095,386 B2 | 1/2012 | Lassetter et al. | |

(Continued)

FOREIGN PATENT DOCUMENTS

| | | |
|---|---|---|
| CN | 102314478 A | 1/2012 |
| CN | 103310398 A | 9/2013 |
| WO | WO 2011/158163 A1 | 12/2011 |

*Primary Examiner* — Truong Vo
(74) *Attorney, Agent, or Firm* — Alston & Bird LLP

(57) ABSTRACT

An apparatus is provided for retrieving information associated with one or more patients. The apparatus includes at least one memory and at least one processor configured to receive queries from devices of health care systems. The queries include data requesting information associated with patients that corresponds to specified items of information indicated in the queries. The queries also indicate a predetermined threshold to determine whether the requested information corresponds to respective patients. The processor is further configured to analyze stored patient information to determine items of the patient information that correspond to the specified items of the information. The processor is further configured to detect a subset of the items of the patient information related to health data that is determined to correspond to a respective patient(s) based on a determined value that equals or exceeds the predetermined threshold. Corresponding computer program products and methods are also provided.

20 Claims, 5 Drawing Sheets

(56) References Cited

U.S. PATENT DOCUMENTS

| | | |
|---|---|---|
| 8,108,311 B2 | 1/2012 | Herlitz |
| 8,126,740 B2 | 2/2012 | Busch |
| 8,135,679 B2 | 3/2012 | Bayliss |
| 8,165,899 B2 | 4/2012 | Yeh et al. |
| 8,200,509 B2 | 6/2012 | Kenedy et al. |
| 8,249,895 B2 | 8/2012 | Faulkner et al. |
| 8,321,383 B2 | 11/2012 | Schumacher et al. |
| 8,321,393 B2 | 11/2012 | Adams et al. |
| 8,332,366 B2 | 12/2012 | Schumacher et al. |
| 8,356,009 B2 | 1/2013 | Ellard et al. |
| 8,359,339 B2 | 1/2013 | Adams et al. |
| 8,370,355 B2 | 2/2013 | Harger et al. |
| 8,370,366 B2 | 2/2013 | Adams et al. |
| 8,417,702 B2 | 4/2013 | Harger et al. |
| 8,423,382 B2 | 4/2013 | Dettinger et al. |
| 8,423,385 B2 | 4/2013 | Radoccia et al. |
| 8,423,514 B2 | 4/2013 | Goldenberg et al. |
| 8,429,220 B2 | 4/2013 | Wilkinson et al. |
| 8,438,182 B2 | 5/2013 | Gillam et al. |
| 8,452,619 B2 | 5/2013 | Kenedy et al. |
| 8,510,129 B2 | 8/2013 | Morris |
| 8,527,295 B2 | 9/2013 | D'Ambrosia |
| 8,620,930 B2 | 12/2013 | Gulhane et al. |
| 8,621,244 B1 | 12/2013 | Rembert et al. |
| 2004/0102998 A1 | 5/2004 | Bao et al. |
| 2006/0080312 A1 | 4/2006 | Friedlander et al. |
| 2008/0228767 A1* | 9/2008 | Kenedy et al. .............. 707/6 |
| 2009/0024417 A1 | 1/2009 | Marks et al. |
| 2009/0089317 A1 | 4/2009 | Ford et al. |
| 2009/0150451 A1 | 6/2009 | Gejdos et al. |
| 2009/0198686 A1 | 8/2009 | Cushman, II et al. |
| 2010/0114877 A1 | 5/2010 | Adams et al. |
| 2010/0131298 A1 | 5/2010 | Buttner et al. |
| 2010/0179834 A1 | 7/2010 | Wager |
| 2011/0010401 A1 | 1/2011 | Adams et al. |
| 2011/0106564 A1 | 5/2011 | Hachmeister et al. |
| 2011/0191349 A1 | 8/2011 | Ford et al. |
| 2011/0246230 A1 | 10/2011 | Sie et al. |
| 2011/0246234 A1 | 10/2011 | Irwin et al. |
| 2011/0246237 A1 | 10/2011 | Vdovjak |
| 2011/0246238 A1 | 10/2011 | Vdovjak et al. |
| 2011/0282688 A1 | 11/2011 | Raggousis |
| 2012/0010904 A1 | 1/2012 | Buck et al. |
| 2012/0059668 A1 | 3/2012 | Baldock et al. |
| 2012/0072237 A1 | 3/2012 | Campbell et al. |
| 2012/0078663 A1 | 3/2012 | Lorsch |
| 2012/0095923 A1 | 4/2012 | Herlitz |
| 2012/0109685 A1 | 5/2012 | Carter et al. |
| 2012/0150887 A1 | 6/2012 | Clark et al. |
| 2012/0203576 A1 | 8/2012 | Bucur et al. |
| 2012/0245954 A1 | 9/2012 | Klotz et al. |
| 2012/0246741 A1 | 9/2012 | Klotz et al. |
| 2013/0080192 A1 | 3/2013 | Bucur et al. |
| 2013/0179186 A1 | 7/2013 | Birtwhistle et al. |
| 2013/0204880 A1 | 8/2013 | Lesiecki et al. |
| 2013/0262141 A1 | 10/2013 | Crockett |
| 2013/0290032 A1 | 10/2013 | Netsch et al. |

* cited by examiner

METHODS, APPARATUSES AND COMPUTER PROGRAM PRODUCTS FOR FACILITATING LOCATION AND RETRIEVAL OF HEALTH INFORMATION IN A HEALTHCARE SYSTEM

TECHNOLOGICAL FIELD

Embodiments of the invention relate generally to healthcare information management and more particularly relate to a method, apparatus and computer program product for accessing and retrieving health information of one or more patients.

BACKGROUND

Currently, health information exchanges (HIEs) facilitate the exchange of healthcare information associated with patients across various organizations within regions, communities or healthcare systems. The healthcare information may be associated with multiple patient records across an HIE. At present, there may be many instances of patient health records relating to a same patient across an HIE. These records may have different identifiers assigned by different assigning authorities such as healthcare systems and in many instances these records may have slightly different demographic data associated with a same patient. The different identifiers and different demographic data associated with patients may create difficulties in retrieving health information about a patient(s).

Further complicating matters is that sometimes two different patients may have the same or similar demographic information. As such, existing record locator search techniques using standard demographic information may not return all of the healthcare information associated with a patient due to discrepancies in demographic from different systems. Another drawback of existing record locator search techniques using standard demographic information is that these techniques may return false positives as being unable to match enough demographic data with a corresponding patient.

Existing record locator search techniques typically attempt to query health information exchange systems for patient records using standard demographic information such as first name, last name, date of birth, gender, or address information of a patient. A problem with this approach is that in many instances too many partial matches occur due to slight discrepancies between the data of multiple systems associated with a patient or false positives may occur because of erroneous matches of patient information across a large number of patients.

Additionally, some existing record locator search techniques attempt to further refine the queries by adding information such as driver license numbers, phone numbers, or social security numbers of patients in order to utilize this information to retrieve health information (e.g., patient health records) associated with corresponding patients. A problem with this approach is that many healthcare systems participating in health information exchange are unable to obtain this information from their patients. As such, in many instances this additional information may not be utilized in search for health information of patients.

For example, one healthcare system such as a clinic may obtain patient identification information such as a driver license number of a patient upon the patient registering with the clinic. However, two other health care systems such as two other clinics may not obtain the driver license number of the same patient when the patient registers with the two clinics during separate patient visits. As such, existing record locator search techniques may be unable to utilize the driver license number of the patient to identify the patient and to identify health information related to the patient.

In view of the foregoing drawbacks, it may be beneficial to provide an efficient and reliable mechanism for accessing and retrieving health information associated with one or more patients.

BRIEF SUMMARY

A method, apparatus and computer program product are therefore provided that may enable provision of an efficient and reliable mechanism for accessing and retrieving health information of one or more patients. The health information of the patients may be provided by various disparate healthcare systems.

An example embodiment may utilize clinical information, demographic information and any other suitable data from various disparate healthcare entities of a health information exchange (HIE) system to retrieve health information of a patient and provide a level of confidence that the retrieved information relates to one or more identified patients. The clinical information (also referred to herein as health information, or health data) may include, but is not limited to, information associated with medications (e.g., prescribed medications), allergies, medical problems, medical procedures (e.g., surgeries), medical results (e.g., laboratory tests, radiology exams, etc.), medical diagnoses, health conditions, or any other suitable data associated with a patient(s).

As such, an example embodiment may utilize clinical information associated with patients in part to identify respective patients and/or health information associated with the respective patient(s). In an example embodiment, a network device may facilitate provision of the identified patient(s) and/or identified health information of the patient(s) to one or more devices of different healthcare systems requesting the information.

In one exemplary embodiment, a method for retrieving information associated with one or more patients is provided. The method may include receiving queries from devices of health care systems. The queries may include data requesting information associated with patients that corresponds to specified items of information indicated in the queries. The queries may also indicate a predetermined threshold to determine whether the requested information corresponds to respective patients. The method may also include analyzing stored patient information to determine items of the patient information that correspond to the specified items of the information. The method may also include detecting a subset of the items of the patient information related to health data that is determined to correspond to a respective patient based on a determined value that equals or exceeds the predetermined threshold.

In another exemplary embodiment, an apparatus for retrieving information associated with one or more patients is provided. The apparatus may include a memory and a processor configured to receive queries from devices of health care systems. The queries may include data requesting information associated with patients that corresponds to specified items of information indicated in the queries. The queries may also indicate a predetermined threshold to determine whether the requested information corresponds to respective patients. The processor is further configured to cause the apparatus to analyze stored patient information to determine items of the patient information that correspond to the specified items of the information. The processor is further configured to cause the apparatus to detect a subset of the items of the patient information related to health data that is determined to correspond to a respective patient based on a determined value that equals or exceeds the predetermined threshold.

In another exemplary embodiment, a computer program product for retrieving information associated with one or more patients is provided. The computer program product includes at least one computer-readable storage medium having computer-executable program code instructions stored therein. The computer-executable program code instructions may include program code instructions configured to cause receipt of queries from devices of health care systems. The queries may include data requesting information associated with patients that corresponds to specified items of information indicated in the queries. The queries may also indicate a predetermined threshold to determine whether the requested information corresponds to respective patients. The computer program product may further include program code instructions configured to analyze stored patient information to determine items of the patient information that correspond to the specified items of the information. The computer program product may further include program code instructions configured to detect a subset of the items of the patient information related to health data that is determined to correspond to a respective patient based on a determined value that equals or exceeds the predetermined threshold.

BRIEF DESCRIPTION OF THE SEVERAL VIEWS OF THE DRAWINGS

Figure 1:
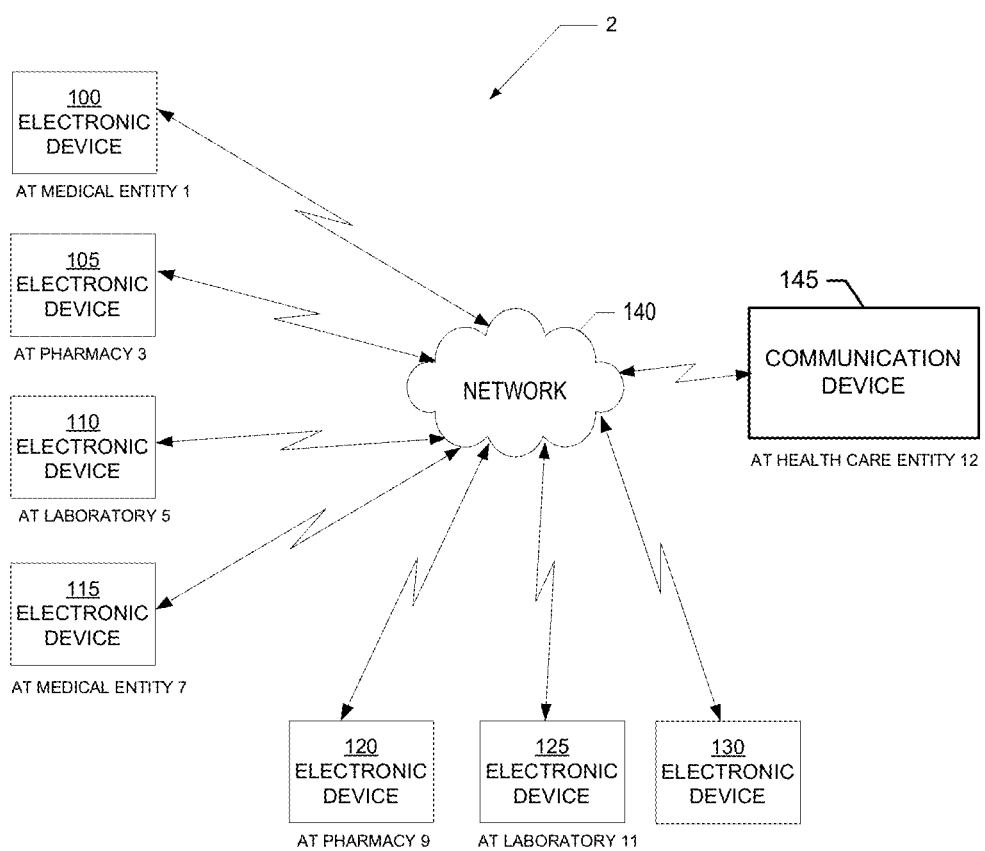
Figure 2:
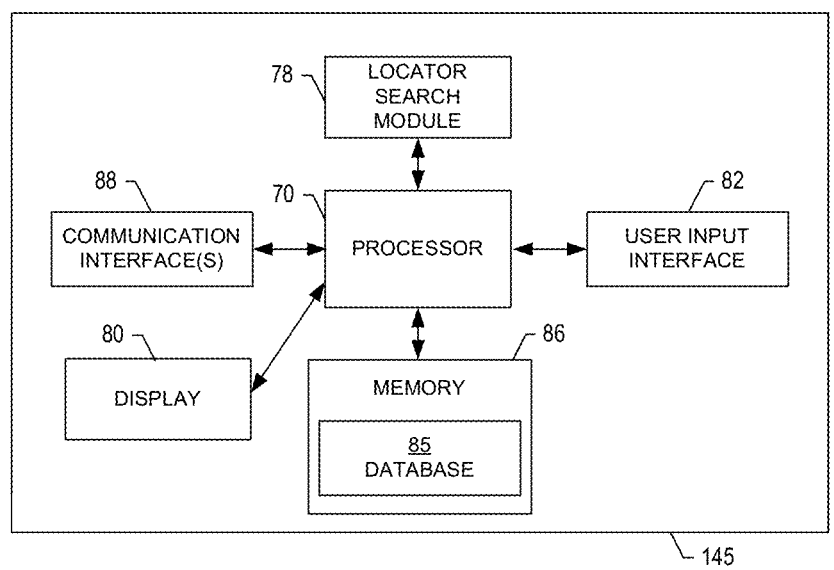
Figure 3:
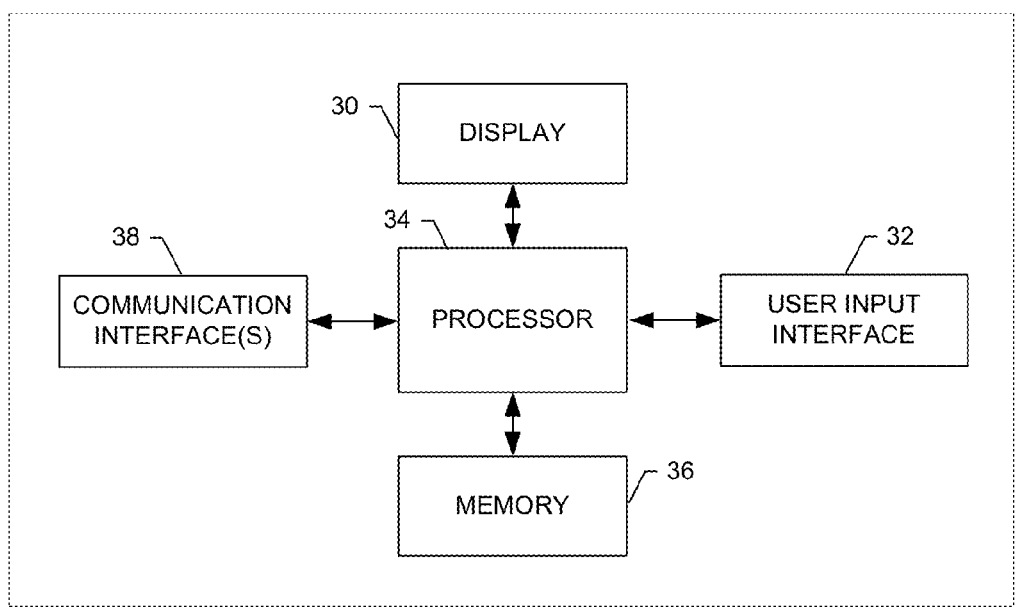
Figure 4:
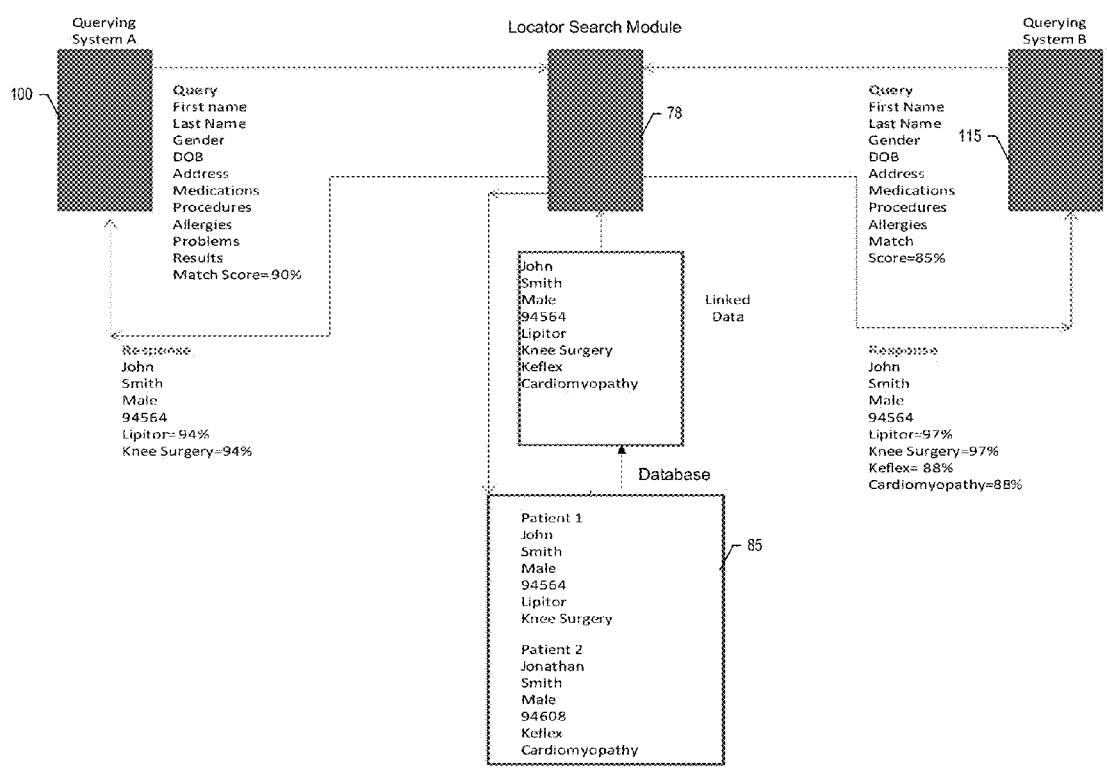
Figure 5:
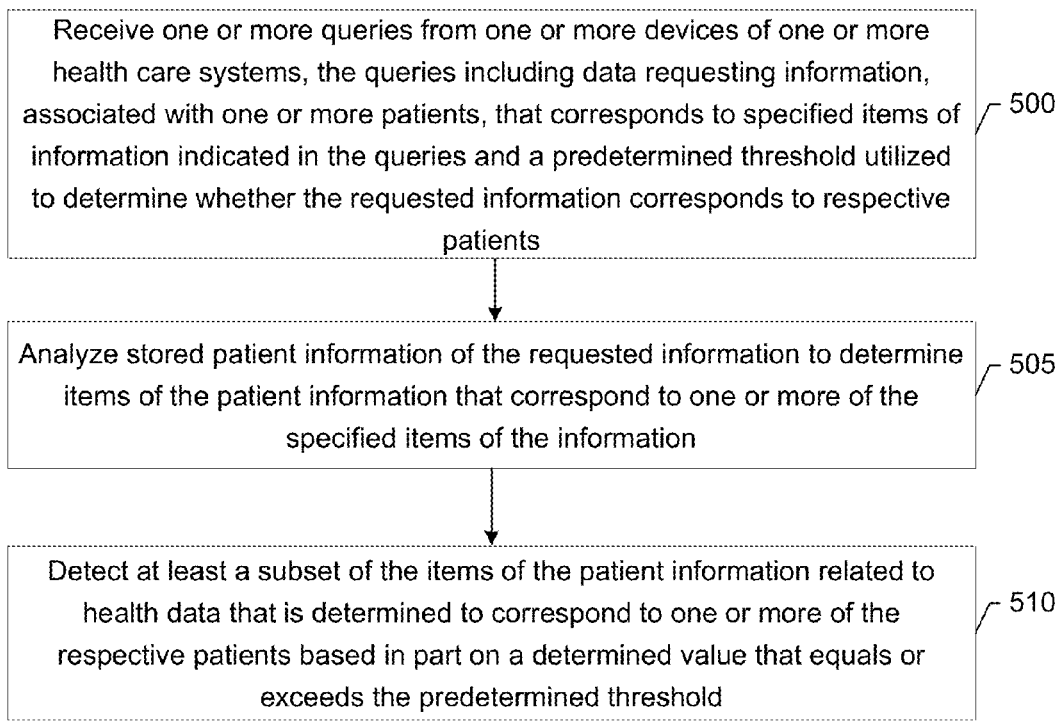

Having thus described the invention in general terms, reference will now be made to the accompanying drawings, which are not necessarily drawn to scale, and wherein:

FIG. 1 is a schematic block diagram of a system according to an exemplary embodiment of the invention;

FIG. 2 is a schematic block diagram of communication device according to an exemplary embodiment of the invention;

FIG. 3 is a schematic block diagram of a computing device according to an exemplary embodiment of the invention;

FIG. 4 is a diagram of a system for retrieving information associated with one or more patients according to an exemplary embodiment of the invention; and FIG. 5 is a flowchart of an exemplary method for retrieving information associated with one or more patients according to an exemplary embodiment of the invention.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein. Like reference numerals refer to like elements throughout. As used herein, the terms "data," "content," "information" and similar terms may be used interchangeably to refer to data capable of being transmitted, received and/or stored in accordance with embodiments of the invention. Moreover, the term "exemplary", as used herein, is not provided to convey any qualitative assessment, but instead merely to convey an illustration of an example. Thus, use of any such terms should not be taken to limit the spirit and scope of embodiments of the invention.

As defined herein a "computer-readable storage medium," which refers to a non-transitory, physical or tangible storage medium (e.g., volatile or non-volatile memory device), may be differentiated from a "computer-readable transmission medium," which refers to an electromagnetic signal.

General System Architecture

Reference is now made to FIG. 1, which is a block diagram of a system according to exemplary embodiments. As shown in FIG. 1, the system 2 (e.g., an HIE system) may include one or more electronic devices 100, 105, 110, 115, 120, 125 and 130 (e.g., personal computers, laptops, workstations, servers, personal digital assistants, smart devices and the like, etc.) which may access one or more network entities such as, for example, a communication device 145 (e.g., a server), or any other similar network entity, over a network 140, such as a wired local area network (LAN) or a wireless local area network (WLAN), a metropolitan network (MAN) and/or a wide area network (WAN) (e.g., the Internet). In this regard, the communication device 145 is capable of receiving data from and transmitting data to the electronic devices 100, 105, 110, 115, 120, 125 and 130 via network 140. In one exemplary embodiment, the electronic devices 100, 105, 110, 115, 120, 125 may be utilized by clinicians, nurses, pharmacists, physicians, physical therapists, laboratory technicians and/or any other suitable health care professionals.

The electronic devices 100, 105, 110, 115, 120, 125 may be maintained by one or more healthcare institutions. For instance, the electronic device 100 may be maintained by a medical entity 1 (e.g., a hospital, clinic, surgical center, etc.), the electronic device 105 may be maintained by a pharmacy 3, the electronic device 110 may be maintained by the laboratory 5. Additionally, the electronic device 115 may be maintained by a medical entity 7 (e.g., a hospital, clinic, surgical center, etc.), the electronic device 120 may be maintained by a pharmacy 9 and the electronic device 125 may be maintained by the laboratory 11. The electronic device 130 may be utilized by one or more patients. In an exemplary embodiment, the communication device 145 may be maintained by a health care entity 12. In an alternative exemplary embodiment, the communication device 145 may be maintained by any other suitable entity.

The communication device 145 may communicate with the electronic devices 100, 105, 110, 115, 120, 125, 130. In this regard, the communication device 145 may receive medical information from and may transmit medical information to the electronic devices 100, 105, 110, 115, 120, 125, 130. For instance, the electronic devices 100, 105, 110, 115, 120, 125 may send the communication device 145 information corresponding to patients associated with the health care institutions (also referred to herein as healthcare systems) of the electronic devices 100, 105, 110, 115, 120, 125. The information sent by the electronic devices 100, 105, 110, 115, 120, 125 to the communication device 145 may include demographic information of respective patients, clinical information associated with the patients and any other suitable information. The demographic information may include, but is not limited to, names of patients, gender of patients, a date of birth of patients, an age of patients, citizenship/nationality information of patients, addresses of patients (e.g., zip codes of addresses), phone numbers of patients, email addresses of patients and any other suitable information.

The clinical data (also referred to herein as health data or health information) may include, but is not limited to, medications of patients, procedures (also referred to herein as medical procedures) (e.g., laboratory tests, surgeries, radiology exams, etc.), indications of allergies of patients, problems (also referred to herein as medical problems) (e.g., medical conditions), diagnoses of patients, medical record numbers of patients, and any other suitable clinical data.

The information provided by the electronic devices to the communication device 145 may also include, but is not limited to, driver license numbers of patients, social security numbers of patients, or other identifiers. Some of the information provided by the electronic devices to the communication device 145 may relate to the same patients. For purposes of illustration and not of limitation, patient John Doe (e.g., a fictitious patient) may receive prescribed medications from one or more of pharmacies 3 and 9 and may be examined by one or more physicians of medical entity 1 and/or medical entity 7. As such, the electronic devices 100, 115 of the medical entities 1 and 7, respectively, may send information (e.g., medical procedures, medical diagnoses, demographic data, etc.) associated with patient John Doe to the communication device 145. Additionally, the electronic devices 105, 120 of the pharmacies 3 and 9, respectively, may send information (e.g., indications of prescribed medications) associated with patient John Doe to the communication device 145. As another example, each of the laboratories 5, 11 may perform medical tests on behalf of a patient Jane Doe (e.g., a fictitious patient). As such, the electronic devices 110, 125 of the laboratories 5, 11, respectively, may send indications of the medical tests and associated demographic data (e.g., names, dates of birth, etc.) to the communication device 145.

Additionally, in an example embodiment, one or more patients may utilize the electronic device to send information (e.g., demographic data, clinical data, other data (e.g., a driver license number(s), a social security number(s), etc.) to the communication device 145 regarding the patients. The communication device 145 may link the data of corresponding patients (e.g., John Doe, Jane Doe) received from the various electronic devices of the healthcare institutions and/or respective patients and may store linked data in a memory device. In response to receipt of a request for the identity of a patient(s) and/or healthcare information of a patient(s) from one or more requesting electronic devices, the communication device 145 may provide the requested identity of the patient(s) and/or the healthcare information with a level of confidence to the respective requesting electronic devices, as described more fully below.

It should be pointed out that although FIG. 1 shows seven electronic devices 100, 105, 110, 115, 120, 125, 130 and one communication device 145 any suitable number of electronic devices 100, 105, 110, 115, 120, 125, 130 and communication devices 145 may be part of the system of FIG. 1 without departing from the spirit and scope of the invention.

Communication Device

FIG. 2 illustrates a block diagram of a communication device according to an exemplary embodiment of the invention. The communication device 145 may, but need not, be a network entity such as, for example, a server. The communication device 145 includes various means for performing one or more functions in accordance with exemplary embodiments of the invention, including those more particularly shown and described herein. It should be understood, however, that one or more of the communication devices may include alternative means for performing one or more like functions, without departing from the spirit and scope of the invention. More particularly, for example, as shown in FIG. 2, the communication device 145 may include a processor 70 connected to a memory 86 (also referred to herein as memory device 86). The memory 86 may comprise volatile and/or non-volatile memory, and typically stores content (e.g., media content), data, information (e.g., medical information, demographic patient information, etc.) or the like.

For example, the memory 86 may store content transmitted from, and/or received by, the electronic devices 100, 105, 110, 115, 120, 125 and 130. In this regard, in an exemplary embodiment, the memory 86 may store data received from various disparate sources. For example, the memory 86 may store medical information (e.g., clinical data), demographic information (e.g. patient demographic data) and/or other data (e.g., a driver license number(s), social security number(s), other identifiers) received by the communication device 145 from the electronic devices of the medical entity 1, the pharmacy 3, the laboratory 5, the medical entity 7, the pharmacy 9 and the laboratory 11. The memory 86 may also store medical information, demographic data and/or other data (e.g., a driver license number(s), social security number(s), other identifiers, etc.) received from the electronic device 130. In an example embodiment, the information received from the electronic devices 100, 105, 110, 115, 120, 125, 130 by the communication device 145 may optionally be stored in a database 85 of the memory 86.

Also for example, the memory 86 typically stores client applications, instructions, algorithms or the like for execution by the processor 70 to perform steps associated with operation of the communication device 145 in accordance with embodiments of the invention. As explained below, for example, the memory 86 may store one or more client applications such as, for example, software (e.g., software code also referred to herein as computer code).

The processor 70 may be embodied in a variety of ways. For instance, the processor 70 may be embodied as a controller, coprocessor microprocessor of other processing devices including integrated circuits such as, for example, an application specific integrated circuit (ASIC), a field programmable gate array (FPGA). In an exemplary embodiment, the processor may execute instructions stored in the memory 86 or otherwise accessible to the processor 70.

The communication device 145 may include one or more logic elements for performing various functions of one or more client applications. In an exemplary embodiment, the communication device 145 may execute the client applications. The logic elements performing the functions of one or more client applications may be embodied in an integrated circuit assembly including one or more integrated circuits (e.g., an ASIC, FPGA or the like) integral or otherwise in communication with a respective network entity (e.g., computing system, client, server, etc.) or more particularly, for example, a processor 70 of the respective network entity.

In addition to the memory 86, the processor 70 may also be connected to at least one interface or other means for displaying, transmitting and/or receiving data, content or the like. The interface(s) can include at least one communication interface 88 or other means for transmitting and/or receiving data, content or the like. In this regard, the communication interface 88 may include, for example, an antenna and supporting hardware and/or software for enabling communications with a wireless communication network. For example, the communication interface(s) may include a first communication interface for connecting to a first network, and a second communication interface for connecting to a second network. In this regard, the communication device is capable of communicating with other devices such as, for example, electronic devices 100, 105, 110, 115, 120, 125 130 over one or more networks (e.g., network 140) such as a Local Area Network (LAN), wireless LAN (WLAN), Wide Area Network (WAN), Wireless Wide Area Network (WWAN), the Internet, or the like. Alternatively, the communication interface can support a wired connection with the respective network.

In addition to the communication interface(s), the interface(s) may also include at least one user interface that may include one or more earphones and/or speakers, a display 80, and/or a user input interface 82. The user input interface, in turn, may comprise any of a number of devices allowing the entity to receive data from a user, such as a microphone, a keypad, keyboard, a touch display, a joystick, image capture device, pointing device (e.g., mouse), stylus or other input device.

In an exemplary embodiment, the processor 70 may be in communication with and may otherwise control a locator search module 78. The locator search module 78 may be any means such as a device or circuitry operating in accordance with software or otherwise embodied in hardware or a combination of hardware and software thereby configuring the device or circuitry (e.g., a processor, controller, microprocessor or the like) to perform the corresponding functions of the locator search module 78, as described below. In examples in which software is employed, a device or circuitry (e.g., processor 70 in one example) executing the software forms the structure associated with such means. As such, for example, the locator search module 78 may be configured to, among other things, receive one or more requests (also referred to herein as queries) from one or more of the electronic devices 100, 105, 110, 115, 120, 125, 130 for data corresponding to a patient(s) (e.g., John Doe, Jane Doe, etc.). In this regard, the locator search module 78 may analyze information that the communication device 145 may have regarding the patient(s) in order to provide the information to the requesting electronic devices regarding the patient(s). The information that the communication device 145 may have regarding the patient(s) may be previously received from the electronic devices 100, 105, 110, 115, 120, 125, 130 of the disparate sources (e.g., healthcare institutions, a patient(s)).

The locator search module 78 may analyze a memory (e.g., memory 86) for possible matches relating to the corresponding patient(s) based in part on utilizing clinical information (e.g., health information) as supplemental data to demographic data to determine whether a corresponding patient(s) matches the information of a request from one or more electronic devices. The locator search module 78 may dynamically determine different confidence levels of a matching patient(s) based on predetermined confidence levels (also referred to herein as predetermined match scores) (e.g., predetermined values ≥90%, ≥85%) designated by the requesting electronic devices.

In this regard, the locator search module 78 may aggregate the data received from electronic devices of disparate sources matching a patient(s) to generate a display of a record that may be sent to a requesting electronic device(s). The aggregated data may include different items of health data assigned a determined weighted score(s) (e.g., the predetermined match score(s)) as to the level of confidence the locator search module 78 is that the health data is associated with the patient(s) identified by the requesting electronic device(s) In addition, the locator search module 78 may not merge data (e.g., medical information associated with different accounts) of different patients and as such data of a health care institution(s) (e.g., medical entity 1) may not be overwritten by data of another healthcare institution (e.g., medical entity 7).

Computing Device

Referring now to FIG. 3, a block diagram of a computing device according to an exemplary embodiment is provided. The computing device is capable of operating as any of electronic devices 100, 105, 110, 115, 120, 125 and 130. In this regard, the electronic devices 100, 105, 110, 115, 120, 125 and 130 may comprise the elements of the computing device of FIG. 3. As shown in FIG. 3, the computing device may include a processor 34 connected to a memory device 36. The memory 36 (also referred to herein as memory device 36) may comprise volatile and/or non-volatile memory, and may store content, information, data or the like. For example, the memory device 36 typically stores content transmitted from, and/or received by, the computing device. Additionally, the memory device 36 may store client applications, software (e.g., software code) algorithms, instructions or the like for the processor 34 to perform steps associated with operation of the computing device. The memory device 36 may store medical information (e.g., clinical data, demographic data, other data (e.g., identifiers (e.g., a driver license number(s), social security number(s), etc.))) associated with one or more patients.

The processor 34 may be embodied in a number of different ways. For example, the processor 34 may be embodied as one or more of various hardware processing means such as a coprocessor, a microprocessor, a controller, a digital signal processor (DSP), or various other processing circuitry including integrated circuits such as, for example, an application specific integrated circuit (ASIC). In an example embodiment, the processor 34 may be configured to execute instructions stored in the memory device 36 or otherwise accessible to the processor 34.

The processor 34 may be connected to at least one communication interface 38 or other means for displaying, transmitting and/or receiving data, content, information or the like. In this regard, the communication interface 38 may be capable of connecting to one or more networks. The computing device may also include at least one user input interface 32 that may include one or more speakers, a display 30, and/or any other suitable devices. For instance, the user input interface 32 may include any of a number of devices allowing the computing device to receive data from a user, such as a keyboard, a keypad, mouse, a microphone, a touch screen display, or any other input device.

The processor 34 may send medical information associated with one or more patients to the communication device 145. Additionally, the processor 34 may generate one or more requests that may be sent to the communication device 145 requesting information pertaining to a corresponding patient(s). The processor 34 may include data in the requests specifying the communication device 145 to provide the computing device with information regarding one or more patients that matches a predetermined level of confidence. The predetermined level of confidence may correspond to a predetermined match score, as described more fully below.

Exemplary System Operation

Exemplary embodiments of the invention may provide an efficient and reliable mechanism for retrieving medical information associated with one or more patients. In this regard, some exemplary embodiments may facilitate receipt of requests from devices of various health care institutions (e.g., medical entity 1, pharmacy 3, laboratory 5, medical entity 7, pharmacy 9, laboratory 11, etc.) or other health care systems requesting additional information (e.g., medical information) regarding one or more patients associated with the health care institutions/systems.

Additionally, the exemplary embodiments may include one or more determined match scores associated with one or more items of medical information indicating a level of confidence that the retrieved information corresponds to one or more identified patients. As such, by analyzing the match scores, a determination may be made as to the reliability of the medical information corresponding to an identified patient(s).

As an example in which the locator search module 78 may retrieve identified medical information associated with one or more patients, consider FIG. 4 described more fully below for purposes of illustration and not of limitation.

Referring now to FIG. 4, a diagram of a system for retrieving information associated with one or more patients according an exemplary embodiment is provided. In the example embodiment of FIG. 4, an electronic device (e.g., electronic device 100) of a querying system A (e.g., medical entity 1) may send the locator search module 78 a query (also referred to herein as a request) requesting patient information from the communication device 145. The query may include data specifying items of information that the electronic device 100 desires to receive from the locator search module 78 for each of the patients in which the communication device 145 stores corresponding patient information.

In the example embodiment of FIG. 4, the query may specify items of information such as, for example, last name, first name, gender, date of birth (DOB), address, medications, procedures (e.g., medical procedures), allergies, problems (e.g., medical problems). However, the query generated by the electronic device 100 may include data specifying any other suitable items of information. Additionally, the query generated by the electronic device 100 may also include an indication of a match score (also referred to herein as a predetermined match score). The predetermined match score may denote to the locator search module 78 to provide the electronic device 100 with specified items of information identified in the query that meet a predetermined threshold (e.g., a predetermined value ≥90%, ≥92%, etc.) indicating a level of confidence, by the locator search module 78, that the specified items of information corresponds to a respective identified patient(s).

In response to receiving the query from the electronic device 100, the locator search module 78 may analyze data in a database 85 of memory 86 and may identify one or more patients that match one or more of the specified items of information included in the received query. In this example embodiment, the locator search module 78 may determine that there is patient information for at least two patients in the database 85 and that the patients have similar names (e.g., John Smith, Jonathan Smith) and the same gender (e.g., male). As shown in FIG. 4, some of the patient information associated with patients John Smith and Jonathan Smith may be linked by the locator search module 78 for providing a response to a received query.

The locator search module 78 may determine that the patient information (e.g., a medical record) indicating the medication Lipitor and the patient information indicating the knee surgery equals or exceeds a match score associated with a predetermined threshold (e.g., the predetermined match threshold (e.g., a predetermined value ≥90%)).

As such, the locator search module 78 may determine that the identified items of specified information requested by the electronic device 100 relating to medications (e.g., Lipitor) and procedures (e.g., knee surgery) correspond to patient 1, namely John Smith (e.g., a fictitious patient). The locator search module 78 may determine that the identified items of specified information relating to medications and procedures corresponds to patient John Smith since the locator search module 78 determined that these items of identified data equaled or exceeded the predetermined match threshold (e.g., a predefined value ≥90%). For instance, the locator search module 78 determined that the medications (e.g., Lipitor) and procedures (e.g., knee surgery) were detected with a level of confidence as being 94% accurate. In an example embodiment, a determined value that equals or exceeds the predetermined match threshold may denote that items of patient information corresponds to a respective patient(s) or signifies an acceptable level of confidence that the items of patient information corresponds to the respective patient(s).

The locator search module 78 may provide the electronic device 100 of the querying system A with a response indicating the patient(s) (e.g., patient John Smith) associated with one or more items of specified information (e.g., medications, procedures, demographic data (e.g., name, gender, zip code)) that met the predetermined match score designated by the electronic device 100. The response may be provided to the electronic device 100 of the querying system A in a display view (e.g., a view of a record) generated by the locator search module 78. The display view may illustrate the information of the response in an organized, concise and user friendly manner. The display view may be provided by a processor (e.g., processor 34) of the electronic device 100 to a display (e.g., display 30). In this regard, the display of the electronic device 110 may show the display view.

Even though the locator search module 78 may detect Keflex and cardiomyopathy associated with patient 2, Jonathan Smith, as potential candidate data for providing to the electronic device 100, the locator search module 78 may not provide this data to the electronic device 100 since location search module 78 may determine that this data does not meet the predetermined match threshold specified by the electronic device 100. For example, the location search module 78 may determine that the Keflex match score is 88% and that the cardiomyopathy match score is 88% as described more fully below. In an example embodiment, in an instance in which the location search module 78 detects that a determined value is below the predetermined threshold this may denote that items of patient information does not correspond to one or more respective patients or it may signify an unacceptable level of confidence that items of patient information corresponds to a respective patient(s).

Additionally, in the example embodiment of FIG. 4, an electronic device (e.g., electronic device 115) of querying system B (e.g., medical entity 7) may generate a query that is sent by a processor 34 of the electronic device 115 to the locator search module 78. The query may include data specifying items of information that the electronic device 115 desires to receive from the communication device 145 for patients in which the device 145 stores corresponding patient information matching the specified items of information. The specified items of information included in the query may include, but are not limited to, first name, last name, gender, dates of birth, address, medications, procedures (e.g., medication procedures), allergies and any other suitable information. The query generated by electronic device 115 may also include a match score (e.g., a predetermined match threshold) indicating to the locator search module 78 to provide items of the specified data for patients that equal or exceed a predetermined threshold (e.g., a predefined value ≥85%) associated with the match score. The predetermined threshold indicates a level of confidence by the locator search module 78 that the specified items of information correspond to a patient(s).

In response to receipt of the query by the locator search module 78, the locator search module 78 may analyze data of the database 85 and determine whether patient information associated with one or more patients stored in the database 85 corresponds to the specified items of information in the received query and equals or exceeds a predetermined threshold of the match score. In this example embodiment, the locator search module 78 may determine that items of information such as, for example, Lipitor, knee surgery, Keflex and cardiomyopathy that matches or corresponds to specified items of information in the query equals or exceeds the predetermined threshold (e.g., a predetermined threshold value ≥85%) associated with the match score. In this example embodiment, the location search module 78 may determine that it detected Lipitor with a 97% match as corresponding to patient John Smith and detected knee surgery with a 97% match as corresponding to patient John Smith. Additionally, the location search module 78 may determine that it detected Keflex with an 88% match as corresponding to patient John Smith and detected cardiomyopathy with an 88% match as corresponding to patient John Smith.

As such, the locator search module 78 may send the electronic device 115 of the querying system B a response including information indicating one or more identified specified items of information such as the Lipitor, knee surgery, Keflex and cardiomyopathy information, the corresponding match scores as well as an indication of a patient(s) (e.g., John Smith) and associated demographic data (e.g., a gender, zip code, etc.) that the locator search module 78 determines that this information corresponds to or matches. In an example embodiment, the locator search module 78 may provide the information of the response to the electronic device 115 in a display view. A processor of the electronic device 115 may provide the display view to a display (e.g., display 30) to enable the display to show the display view.

In the example embodiment of FIG. 4, although the locator search module 78 determined that the Keflex and cardiomyopathy corresponds to patient John Smith, the corresponding match scores of 88% may indicate to the electronic device 115 that the locator search module 78 is less confident that the matches of the Keflex and cardiomyopathy corresponds to patient John Smith. In this regard, for example, as shown in the data of the database 85, the Keflex information and cardiomyopathy information correspond to patient Jonathan Smith. On the other hand, the match scores of 97% associated with Lipitor and knee surgery may denote to the electronic device 115 that the location search module 78 has a high level of confidence that the Lipitor and knee surgery information corresponds to patient John Smith.

Referring now to FIG. 5, an exemplary method of retrieving one or more items of information associated with one or more patients is provided. At operation 500, an apparatus (e.g., communication device 145) may receive one or more queries from one or more devices (e.g., electronic devices 100, 105, 110, 115, 120, 125) of one or more health care systems (e.g., medical entity 1, pharmacy 3, laboratory 5, medical entity 7, pharmacy 9, laboratory 11, etc.). In one example embodiment, the apparatus (e.g., communication device 145) may also receive a query from an electronic device 130. The queries may include data requesting information, associated with one or more patients, which correspond to specified items of information indicated in the queries. The queries also indicate a predetermined threshold (e.g., a match score (e.g., a predetermine threshold value ≥90%)) utilized to determine whether the requested information corresponds to respective patients.

At operation 505, an apparatus (e.g., communication device 145) may analyze stored patient information (e.g., patient information stored in database 85) of the requested information to determine items of the patient information that correspond to the specified items of the information. The specified items of information may include but are not limited to first name, last name, gender, date of birth, address, medications, medical procedures, allergies, medical problems, medical results, medical diagnoses of a patient and any other suitable patient information. At operation 510, an apparatus (e.g., communication device 145) may detect at least a subset of the items of the patient information (e.g., medications, medical procedures) related to health data that is determined to correspond to one or more of the respective patients (e.g., John Smith, Jonathan Smith, etc.) based in part on a determined value (e.g., 94%) that equals or exceeds the predetermined threshold.

It should be pointed out that FIG. 5 is a flowchart of a system, method and computer program product according to exemplary embodiments of the invention. It will be understood that each block or step of the flowchart, and combinations of blocks in the flowchart, can be implemented by various means, such as hardware, firmware, and/or a computer program product including one or more computer program instructions. For example, one or more of the procedures described above may be embodied by computer program instructions. In this regard, in an example embodiment, the computer program instructions which embody the procedures described above are stored by a memory device (e.g., memory 86, memory 36) and executed by a processor (e.g., processor 70, processor 34, locator search module 78). As will be appreciated, any such computer program instructions may be loaded onto a computer or other programmable apparatus (e.g., hardware) to produce a machine, such that the instructions which execute on the computer or other programmable apparatus cause the functions specified in the flowchart blocks or steps to be implemented. In some embodiments, the computer program instructions are stored in a computer-readable memory that can direct a computer or other programmable apparatus to function in a particular manner, such that the instructions stored in the computer-readable memory produce an article of manufacture including instructions which implement the function specified in the flowchart blocks or steps. The computer program instructions may also be loaded onto a computer or other programmable apparatus to cause a series of operational steps to be performed on the computer or other programmable apparatus to produce a computer-implemented process such that the instructions which execute on the computer or other programmable apparatus provide steps for implementing the functions specified in the flowchart blocks or steps.

Accordingly, blocks or steps of the flowchart support combinations of means for performing the specified functions and combinations of steps for performing the specified functions. It will also be understood that one or more blocks or steps of the flowchart, and combinations of blocks or steps in the flowchart, can be implemented by special purpose hardware-based computer systems which perform the specified functions or steps, or combinations of special purpose hardware and computer instructions.

In an exemplary embodiment, an apparatus for performing the methods of FIG. 5 above may comprise a processor (e.g., the processor 70, the processor 34, the locator search module 78) configured to perform some or each of the operations described above. The processor may, for example, be configured to perform the operations by performing hardware implemented logical functions, executing stored instructions, or executing algorithms for performing each of the operations. Alternatively, the apparatus may comprise means for performing each of the operations described above. In this regard, according to an example embodiment, examples of means for performing operations may comprise, for example, the processor 34, the processor 70 (e.g., as means for performing any of the operations described above), the locator search module 78 and/or a device or circuit for executing instructions or executing an algorithm for processing information as described above.

CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method comprising:
   receiving a query from a device associated with a health care system for health care information associated with a patient, the query comprising (a) one or more specified items of information associated with the patient, the specified items of information comprising demographic and clinical data associated with the patient, and (b) a predetermined threshold to be used to determine whether the requested information corresponds to the patient;
   analyzing stored patient information received from a plurality of health care systems, the patient information comprising demographic and clinical data associated with a plurality of patients to identify items of the patient information that correspond to one or more of the specified items of information; and
   detecting, via a processor, at least a subset of the items of patient information that is determined to correspond to the patient based in part on a determined value that equals or exceeds the predetermined threshold, wherein the determined value comprises a calculated score indicating a level of confidence that the subset of the items of patient information corresponds to the patient.

2. The method of claim 1, further comprising:
   enabling provision of one or more generated responses to the device comprising content indicating the patient and the items of patient information associated with a respective determined score indicating a confidence that the items of patient information correspond to the patient.

3. The method of claim 2, wherein prior to enabling provision, the method further comprises:
   identifying one or more candidate items of the patient information; and
   excluding the candidate items from the responses based in part on detecting that another determined value is below the predetermined threshold.

4. The method of claim 3, wherein detecting that the another determined value is below the predetermined threshold denotes that the subset of items of patient information does not correspond to the patient or signifies an unacceptable level of confidence that the subset of the items of patient information corresponds to the patient.

5. The method of claim 1, wherein the determined value that equals or exceeds the predetermined threshold denotes that the subset of items of patient information corresponds to the patient or signifies an acceptable level of confidence that the subset of the items of patient information corresponds to the patient.

6. The method of claim 2, further comprising:
   arranging the content of the responses in respective medical records to enable the device to display the records.

7. The method of claim 1, wherein prior to receiving the query the method further comprises:
   receiving the patient information from one or more devices associated with the plurality of health care systems.

8. The method of claim 1, wherein the clinical data comprises at least one of a medication, a health procedure, an allergy, a health problem, or a medical diagnosis of the patient.

9. The method of claim 1, wherein the clinical data corresponds to a health condition of the patient.

10. An apparatus comprising:
    at least one memory; and
    at least one processor configured to cause the apparatus to:
       receive a query from a device associated with a health care system for health care information associated with a patient, the query comprising (a) one or more specified items of information associated with the patient, the specified items of information comprising demographic and clinical data associated with the patient, and (b) a predetermined threshold to be used to determine whether the requested information corresponds to the patient;
       analyze stored patient information received from a plurality of health care systems, the patient information comprising demographic and clinical data associated with a plurality of patients to identify items of the patient information that correspond to one or more of the specified items of information; and
       detect at least a subset of the items of patient information that is determined to correspond to the patient based in part on a determined value that equals or exceeds the predetermined threshold, wherein the determined value comprises a calculated score indicating a level of confidence that the subset of the items of patient information corresponds to the patient.

11. The apparatus of claim 10, wherein the processor is further configured to cause the apparatus to:
    enable provision of one or more generated responses to the device comprising content indicating the patient and the items of patient information associated with a respective determined score indicating a confidence that the items of patient information correspond to the patient.

12. The apparatus of claim 11, wherein prior to enable provision, the processor is further configured to cause the apparatus to:
    identify one or more candidate items of the patient information; and
    exclude the candidate items from the responses based in part on detecting that another determined value is below the predetermined threshold.

13. The apparatus of claim 12, wherein detecting that the another determined value is below the predetermined threshold denotes that the subset of items of patient information does not correspond to the patient or signifies an unacceptable level of confidence that the subset of the items of patient information corresponds to the patient.

14. The apparatus of claim 10, wherein the determined value that equals or exceeds the predetermined threshold denotes that the subset of items of patient information corresponds to the patient or signifies an acceptable level of confidence that the subset of the items of patient information corresponds to the patient.

15. The apparatus of claim 11, wherein the processor is further configured to cause the apparatus to:
arrange the content of the responses in respective medical records to enable the device to display the records.

16. The apparatus of claim 10, wherein prior to receive the query the processor is further configured to cause the apparatus to:
receive the patient information from one or more devices associated with the plurality of health care systems.

17. The apparatus of claim 10, wherein the clinical data comprises at least one of a medication, a health procedure, an allergy, a health problem, or a medical diagnosis of the patient.

18. The apparatus of claim 10, wherein the clinical data corresponds to a health condition of the patient.

19. A computer program product comprising at least one non-transitory computer-readable storage medium having computer-executable program code instructions stored therein, the computer executable program code instructions comprising:
program code instructions configured to cause receipt of a query from a device associated with a health care system for health care information associated with a patient, the query comprising (a) one or more specified items of information associated with the patient, the specified items of information comprising demographic and clinical data associated with the patient, and (b) a predetermined threshold to be used to determine whether the requested information corresponds to the patient;
program code instructions configured to analyze stored patient information received from a plurality of health care systems, the patient information comprising demographic and clinical data associated with a plurality of patients to identify items of the patient information that correspond to one or more of the specified items of information; and
program code instructions configured to detect at least a subset of the items of patient information that is determined to correspond to the patient based in part on a determined value that equals or exceeds the predetermined threshold, wherein the determined value comprises a calculated score indicating a level of confidence that the subset of the items of patient information corresponds to the patient.

20. The computer program product of claim 19, further comprising:
program code instructions configured to enable provision of one or more generated responses to the device comprising content indicating the patient and the items of patient information associated with a respective determined score indicating a confidence that the items of patient information correspond to the patient.

* * * * *